(12) United States Patent
Hashimoto

(10) Patent No.: US 8,855,733 B2
(45) Date of Patent: Oct. 7, 2014

(54) SUBSTANCE COMPONENT DETECTION DEVICE

(75) Inventor: Nobuaki Hashimoto, Suwa (JP)

(73) Assignee: Seiko Epson Corporation (JP)

( * ) Notice: Subject to any disclaimer, the term of this patent is extended or adjusted under 35 U.S.C. 154(b) by 168 days.

(21) Appl. No.: 13/416,179

(22) Filed: Mar. 9, 2012

(65) Prior Publication Data

US 2012/0238840 A1    Sep. 20, 2012

(30) Foreign Application Priority Data

Mar. 18, 2011  (JP) ................... 2011-061226

(51) Int. Cl.
*A61B 5/1455* (2006.01)
*G01N 21/65* (2006.01)
*A61B 5/00* (2006.01)

(52) U.S. Cl.
CPC ............ G01N 21/658 (2013.01); A61B 5/0075 (2013.01); A61B 5/1455 (2013.01)
USPC ........................... 600/310; 356/301; 73/31.05

(58) Field of Classification Search
CPC ............. A61B 5/14546; A61B 5/1455; A61B 5/0059; A61B 5/0075; G01N 21/658; G01N 21/65; G01N 27/407; C12Q 2565/632
USPC .......... 600/309, 310; 356/301; 73/23.2, 31.05
See application file for complete search history.

(56) References Cited

U.S. PATENT DOCUMENTS 8,223,331 B2 *  7/2012  Bratkovski et al. ........... 356/301
2011/0198501 A1   8/2011  Ouchi et al.

FOREIGN PATENT DOCUMENTS

| JP | 10-239309    | 9/1998  |
| JP | 2006-214747  | 8/2006  |
| JP | 2009-175111  | 8/2009  |
| JP | 2009-201661  | 9/2009  |
| JP | 2010-107414  | 5/2010  |
| JP | 2010-148692  | 7/2010  |
| JP | 2010-169658  | 8/2010  |
| JP | 2010-320353  | 10/2010 |
| JP | 2010-281698  | 12/2010 |

* cited by examiner

*Primary Examiner* — Eric Winakur
(74) *Attorney, Agent, or Firm* — Harness, Dickey & Pierce, P.L.C.

(57) ABSTRACT

A substance component detection device includes a sensor substrate which is provided inside a concave groove, in which when an opening is closed by a measurement-target skin to form a closed space, and includes a projection group having a plurality of projections, a light source section which emits light toward the projection group, and light-receiving section which detects Raman scattering light generated by the projection group.

9 Claims, 5 Drawing Sheets

SUBSTANCE COMPONENT DETECTION DEVICE

BACKGROUND

1. Technical Field

The present invention relates to a substance component detection device which detects a substance component (target substance) in skin gas transpired from skin.

2. Related Art

In the related art, a device is known which detects a substance component included in skin gas transpired from the skin of a person (for example, see JP-A-10-239309).

An alcohol concentration measurement device (substance component detection device) described in JP-A-10-239309 extracts a secretion secreted from the skin by a capsule in close contact with the skin, and analyzes the extracted secretion using a gas chromatograph.

On the other hand, in the substance component detection device described in JP-A-10-239309, an introduction tube which introduces the secretion extracted by the capsule into the gas chromatograph is needed. In order to detect an alcohol component, a large and expensive gas chromatograph is used, causing an increase in device cost and an increase in size.

SUMMARY

An advantage of some aspects of the invention is that it provides a substance component detection device capable of easily detecting a component in skin gas with a simple configuration.

A substance component detection device according to an aspect of the invention includes a sensor substrate which is provided in a closed space of a closed space forming portion, which has at least one opening and in which the opening is closed by the measurement-target skin such that the inside of the closed space forming portion forms the closed space, and has a projection group having a plurality of metal projections, an incidence optical system which emits light toward the projection group, and a light-receiving section which detects Raman scattering light generated by the projection group.

With this aspect of the invention, the opening of the closed space forming portion is closed by the skin, such that the inside of the closed space forming portion becomes the closed space. Inside the closed space are provided the sensor substrate including the projection group having a plurality of metal projections, and the incidence optical system which emits light toward the projection group of the sensor substrate. In this sensor substrate, if light is incident from the incidence optical system, an enhancing electric field is formed between the metal projections of the projection group. If a target substance enters the enhancing electric field, Raman scattering light including information on the frequency of the target substance is generated, and the generated Raman scattering light is enhanced by the enhancing electric field and becomes surface-enhanced Raman scattering light. The surface-enhanced Raman scattering light is detected by the light-receiving section to acquire a Raman spectrum, thereby performing target substance detection and concentration measurement.

In this substance component detection device, for example, a small sensor chip can be used compared to a large-sized device, such as the chromatograph or the like in the related art, thereby achieving reduction in the size of the device. Since the opening of the closed space forming portion is indirect contact with the measurement-target skin, it is not necessary to send skin gas to a detection device through an introduction tube or the like, or to separately extract skin gas by a bag or the like. For example, while the substance component detection device is directly put on the measurement-target skin, skin gas component analysis can be performed.

In the substance component detection device, it is preferred that a seal member which is in close contact with the skin along the opening to seal the closed space is provided in the closed space forming portion.

In this aspect of the invention, the seal member is provided along the opening of the closed space forming portion. With this configuration, when the opening is closed by the skin, the skin is in close contact with the seal member, thereby more reliably preventing leakage of skin gas in the closed space and improving detection precision of a target substance included in skin gas.

In the substance component detection device, it is preferred that the seal member is an elastic member.

In this aspect of the invention, the seal member is constituted by an elastic member. When the seal member is constituted by an elastic member, when the skin is brought into close contact with the seal member, the elastic member is deformed to follow the unevenness of the skin. Therefore, for example, even when the opening is pressed against a wrinkled portion, such as a palm, gaps due to wrinkles can be closed by the elastic member, thereby reliably sealing the closed space.

It is preferred that the substance component detection device further includes a pressing unit which presses the skin against the closed space.

In this aspect of the invention, since the pressing unit is provided, for example, it is not necessary for a user to press and fix the substance component detection device against the skin with his/her hands, thereby easily fixing the substance component detection device to the skin of a measurement-target site. It is also possible to eliminate the gap between the skin and the opening by pressing, thereby preventing leakage of skin gas.

In the substance component detection device, it is preferred that the sensor substrate is provided at an angle crossing an opening surface, which is a surface including the opening edge of the opening.

In this aspect of the invention, the sensor substrate is provided at an angle crossing the opening surface.

With this configuration, the incidence direction of light incident onto the sensor substrate from the incidence optical system can be close to the normal direction of the substrate surface of the sensor substrate.

That is, when the sensor substrate is provided in parallel with respect to the opening surface, and the projection group faces the opening, the incidence optical system or the light-receiving section may not be provided in a surface facing the projection group of the sensor substrate. For this reason, it is necessary to allow light from the incidence optical system to be incident obliquely from the side of the sensor substrate. With this configuration, the incidence angle of light from the incidence optical system with respect to the sensor substrate is small, loss in the amount of light increases, and the intensity of the enhancing electric field is weakened, such that Raman scattering light having strong signal intensity may not be obtained.

In contrast, as in this aspect of the invention, when the sensor substrate is provided at an angle crossing the opening, it is possible to increase the incidence angle of light incident on the sensor substrate from the incidence optical system, and to suppress light loss. Therefore, it is possible to acquire Raman scattering light having strong intensity.

In the substance component detection device, it is preferred that the sensor substrate is provided at an angle equal to or larger than 45 degrees and equal to or smaller than 90 degrees with respect to the opening surface.

It is preferable that the incidence angle of light incident on the projection group of the sensor substrate from the light source section is 90 degrees. As described above, loss in the amount of light decreases, such that the intensity of the enhancing electric field is intensified by the intensity of incident light. Therefore, when the incidence angle of light is 90 degrees, it is possible to minimize loss in the amount of light.

However, when the sensor substrate is at an angle equal to or larger than 0 degree and equal to or smaller than 45 degrees with respect to the opening surface, it becomes difficult to allow light of the light source section to be incident on the sensor substrate at 90 degrees. If an optical member, such as a mirror, is separately used, it is possible to allow light to be incident from a direction perpendicular to the sensor substrate. In this case, however, it is necessary to provide an optical member, causing complexity in the configuration and an increase in the size of the device.

In contrast, in this aspect of the invention, the sensor substrate is formed at an angle equal to or larger than 45 degrees and equal to or smaller than 90 degrees with respect to the opening surface. For this reason, it is possible to easily allow light from the incidence optical system to be incident at an angle perpendicular to the sensor substrate without providing an optical member, such as a mirror, to suppress loss in the amount of light, and to intensify the enhancing electric field.

The term "perpendicular" used herein includes cases where the incidence angle of light is slightly inclined with respect to the normal direction of the sensor substrate. The range of the inclination angle may be set such that loss in the amount of light of the incidence optical system is equal to or smaller than a prescribed value set in advance.

In the substance component detection device, the sensor substrate may be provided in parallel with respect to an opening surface, which is a surface including the opening edge of the opening.

In this aspect of the invention, the sensor substrate is provided in parallel with respect to the opening surface. With this configuration, it is possible to make the depth from the opening in the closed space forming portion small, and to further reduce the size of the substance component detection device.

In the substance component detection device, it is preferred that the sensor substrate is provided in a state where the projection group faces the opening surface.

In this aspect of the invention, the projection group of the sensor substrate is provided to face the opening, and as described above, the sensor substrate is provided in parallel with the opening surface of the opening. With this configuration, the skin closing the opening becomes close to the projection group of the sensor substrate, and the distance between the skin and each metal projection constituting the projection group is made uniform. Therefore, skin gas transpired from the skin easily enters between the metal projections of the projection group, and skin gas can uniformly enter the enhancing electric field formed between the metal projections of the projection group. As a result, it is possible to further improve detection precision of the target substance in skin gas.

In the substance component detection device, the closed space forming portion may include a bottom portion which faces the opening, the sensor substrate may be provided in a state where the projection group faces the bottom portion, a gap through which skin gas transpired from the skin is passable may be provided between the sensor substrate and the bottom portion, and the incidence optical system and the light-receiving section may be provided in the bottom portion.

In this aspect of the invention, as described above, since the sensor substrate is provided in parallel with the opening surface of the opening, it is possible to suppress the thickness of the substance component detection device, and to promote the reduction in size. The incidence optical system and the light-receiving section are in the bottom portion, and light perpendicular to the projection group of the sensor substrate can be incident from the incidence optical system, thereby suppressing loss in the amount of light and intensifying the enhancing electric field. Therefore, it is possible to intensify the intensity of Raman scattering light, thereby further improving detection precision.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Hereinafter, a substance component detection device according to a first embodiment of the invention will be described with reference to the drawings.

1. Overall Configuration of Substance Component Detection Device

Figure 1:
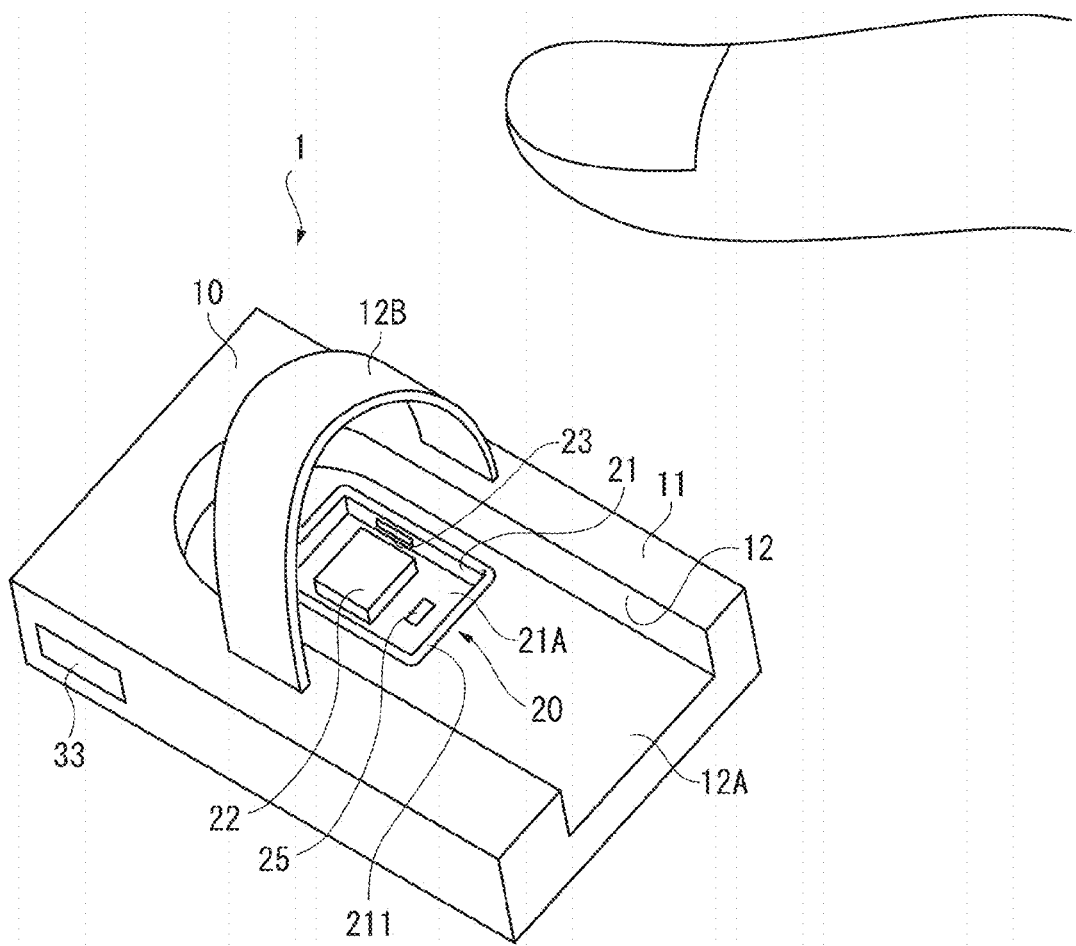
FIG. 1 is a schematic view showing a substance component detection device according to a first embodiment of the invention.

FIG. 1 is a schematic view showing a substance component detection device 1 according to the first embodiment of the invention.

A substance component detection device 1 is a device which is put on a measurement-target finger and detects a target substance in skin gas from skin gas transpired from the skin surface of the finger. The substance component detection device 1 can be used as, for example, a medical instrument or a drinking detection device.

Although in this embodiment, the substance component detection device 1 which can be put on the finger is illustrated, the invention is not limited thereto. For example, the substance component detection device 1 may be put on other sites of a human body, such as a palm or an arm. The site on which the substance component detection device 1 is put is not limited to a human body, and the substance component detection device 1 may be applied as a device which is put on the skin of an animal, such as a pet or a domesticated animal, and detects a component in skin gas transpired from the skin of the animal.

As shown in FIG. 1, the substance component detection device 1 includes a base portion 10, a sensor main body 20 which is provided in the base portion 10, and a control section 30 (see FIG. 4) which controls the sensor main body 20.

The base portion 10 includes a positioning concave portion 12 which positions a finger in a first surface 11, with which the finger is in contact, with respect to a sensor main body 20. As shown in FIG. 1, the positioning concave portion 12 is formed to have a width corresponding to, for example, the forefinger of an ordinary adult.

The sensor main body 20 is provided in a region of a bottom 12A of the positioning concave portion 12, with which the pad portion of the finger is in contact, when a measurement-target person places his/her finger with respect to the positioning concave portion 12.

In order to reliably bring the finger and the sensor main body 20 in close contact with each other, a band 12B (constituting a pressing unit according to the invention) may be provided in the base portion 10. The band 12B is formed of an elastic member, for example, a rubber band, and presses the finger positioned in the positioning concave portion 12 against the sensor main body 20.

The band 12B is not limited to an elastic rubber band, and a band may be used which includes an attachment/detachment portion, such as Magic Tape (Registered Trademark), and presses the finger against the sensor main body 20 to tighten the finger to the sensor main body 20. A band may also be used which presses the finger against the sensor main body 20 with the finger sandwiched by, for example, clips or the like.

2. Configuration of Sensor Main Body

Figure 2:
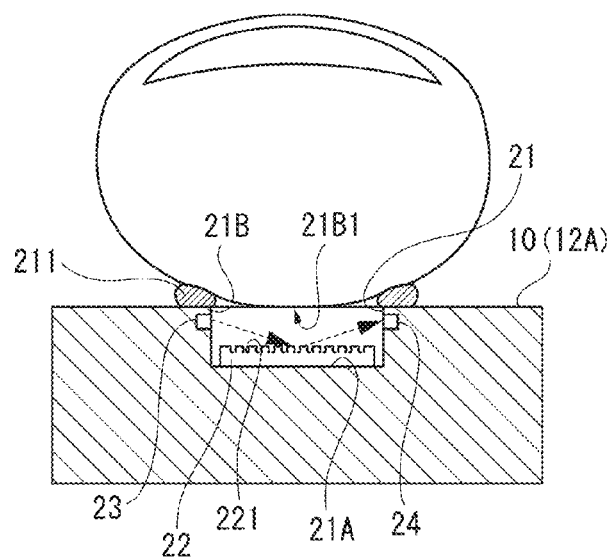
FIG. 2 is a sectional view showing the schematic configuration of a sensor main body of the first embodiment.
Figure 3:
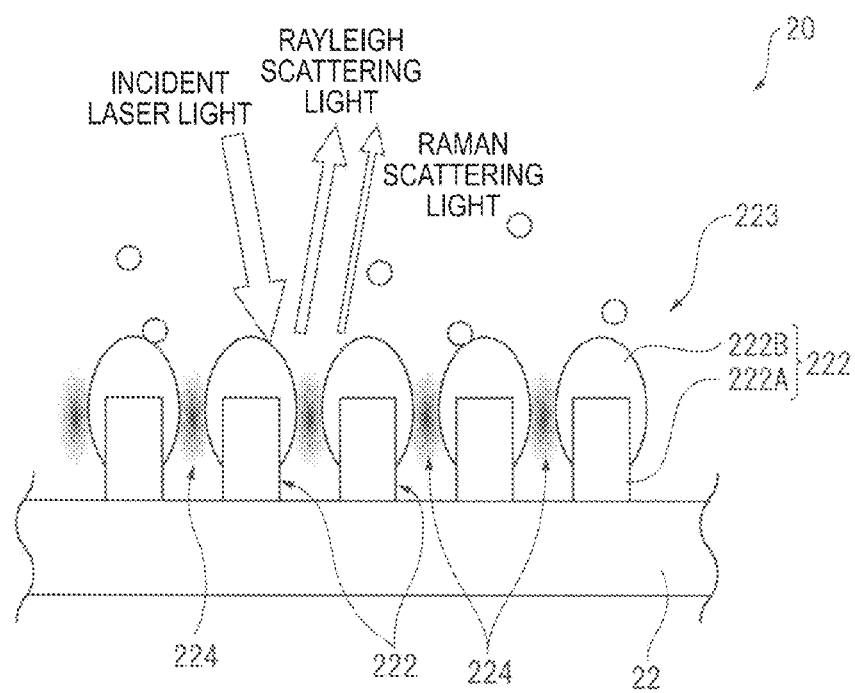
FIG. 3 is an enlarged view showing near a sensor substrate of the sensor main body of the first embodiment on a magnified scale.

FIG. 2 is a sectional view showing the schematic configuration of the sensor main body 20 of the first embodiment. FIG. 3 is an enlarged view showing near a sensor substrate 22 of a sensor main body on a magnified scale.

As shown in FIG. 2, the sensor main body 20 includes a concave groove 21 (constituting a closed space forming portion according to the invention), a sensor substrate 22 which is provided inside the concave groove 21, a light source section 23 (constituting an incidence optical system according to the invention) which emits laser light toward the sensor substrate 22, a light-receiving section 24 which receives scattering light generated by the sensor substrate 22, and a pressure sensor 25 (see FIGS. 1 and 4) which is provided at the bottom 21A of the concave groove 21.

The concave groove 21 is a groove which is formed by further digging the bottom 12A of the positioning concave portion 12 through, for example, etching or the like, and a circular packing member 211 (constituting a seal member according to the invention) is provided along an opening 21B (opening edge). With regard to the concave groove 21, the whole circumference of the opening 21B of the concave groove 21 is closed by the finger of the measurement-target person, such that a closed space is formed by the inside of the concave groove 21 and the finger surface. At this time, the packing member 211 provided over the whole circumference of the opening 21B is in close contact with the finger, such that the closed space becomes a sealed space. Thus, skin gas transpired from the finger surface is sealed in the sealed space. The packing member is an elastic member which is formed of, for example, rubber or the like, and is elastically deformed if the finger is pressed by the band 12B serving as a pressing unit. Therefore, the packing member 211 can be in close contact with the wrinkled portion of the finger, such that the closed space is reliably sealed.

Nonvolatile gel or the like may be applied to the packing member 211 to reliably fill the gap, such as a fingerprint or wrinkles.

The light source section 23 is provided in one lateral surface of the concave groove 21, and emits light as linearly polarized light of a single wavelength toward the sensor substrate 22. In this embodiment, the light source section 23 has a surface-emission laser medium, and emits laser light as linearly polarized light of a single wavelength.

The wavelength of laser light which is oscillated from the light source section 23 can be appropriately set by the type of metal particulates 222B described below. For example, when the metal particulates 222B are gold (Au), the wavelength of laser light can be set to, for example, 633 nm. When the metal particulates 222B are silver (Ag), the wavelength of laser light can be set to, for example, 514 nm. In order to suppress fluorescence of an impurity other than the target substance as a detection target, the wavelength of laser light may be set to, for example, about 780 nm.

The light-receiving section 24 is provided in a lateral surface facing the surface, in which the light source section 23 is provided, from among the lateral surfaces of the concave groove 21. The light-receiving section 24 includes a spectral filter 241 (see FIG. 4) and a light-receiving element 242 (see FIG. 4).

The spectral filter 241 is a filter which cuts light (for example, Rayleigh scattering light)) other than Raman scattering light generated by the sensor substrate 22 and transmits Raman scattering light. As the spectral filter 241, for example, an etalon element or the like may be used. In particular, in the spectral filter 241, when the spectrum at each wavelength is acquired by the light-receiving element 242 while changing the wavelength to transmit, as the spectral filter 241, a wavelength-variable etalon element which can select a wavelength to transmit is preferably used.

The light-receiving element 242 receives light having transmitted the spectral filter 241, and outputs a signal according to the amount of light received to the control section 30.

As shown in FIG. 2, the sensor substrate 22 is a substrate in which, for example, a plurality of slit grooves 221 are formed in a surface facing the opening 21B of the concave groove 21. The slit grooves 221 are set at an interval, for example, from 300 nm to the oscillation wavelength of laser light. The sensor substrate 22 is formed of a size such that each side is, for example, about 5 mm. The sensor substrate 22 is provided such that the surface in which the slit grooves 221 are formed faces the opening surface 21B1 in the opening 21B of the concave groove 21, and is in parallel with respect to the opening surface 21B1.

If a part of the slit grooves 221 of the sensor substrate 22 is enlarged, as shown in FIG. 3, a projection group 223 of a metallic nanostructure constituted by a plurality of projections 222 (metal projections) is formed in the surface of the sensor substrate 22. The projections 222 are constituted by coating the metal particulates 222B (for example, gold, silver, copper, aluminum, palladium, platinum, or the like) on convex portions 222A provided in the surface of the sensor substrate 22. The pitch between the metal particulates 222B in the projections 222 is appropriately set to a size from 1 nm to about half the lattice pitch of the slit grooves 221.

Next, the target substance detection principle of the sensor main body 20 will be described.

The sensor main body 20 is a substance component detection sensor using localized plasmon resonance, and detects the target substance by the following principle.

That is, the metal particulates 222B provided in the sensor main body 20 are formed to be smaller than the wavelength of laser light emitted from the light source section 23. If laser light is irradiated to the metal particulates 222B, laser light acts on the free electrons in the surfaces of the metal particulates 222B, leading to resonance. Thus, electric dipoles by the free electrons are excited inside the metal particulates 222B, and as shown in FIG. 3, an enhancing electric field 224 which is stronger than the electric field of laser light incident between the metal particulates 222B is formed. This phenomenon is the phenomenon specific to the metallic nanostructure smaller than the wavelength of laser light.

In this embodiment, as shown in FIG. 2, a plurality of slit grooves 221 are formed in the sensor substrate 22, and the groove width of the slit grooves 221 is smaller than the laser oscillation wavelength. Thus, an enhancing electric field is formed between the slit grooves 221 and the metal particulates 222B provided in the opposing surfaces of the slit grooves 221. Therefore, a region where the enhancing electric field 224 is formed increases, making it possible to further improve detection precision of the target substance.

If the gap between the metal particulates 222B is small and the height of the projections 222 increases, the enhancing electric field 224 is further intensified. If the intensity of laser light incident from the light source section 23 is intensified, the enhancing electric field 224 is further intensified. Meanwhile, if the gap between the metal particulates 222B is too small, the probability that the target substance enters the gap decreases. Thus, in this embodiment, as described above, it is preferable that the gap between the metal particulates 222B is of a size from 1 nm to half the lattice pitch of the slit grooves 221. When the height of the projections 222 is great, since it takes a lot of time from when the target substance enters the enhancing electric field 224 until the target substance leaves the enhancing electric field 224, it is possible to stably detect Raman scattering light.

The projections 222 may be formed between the opposing surfaces of the slit grooves 221. In this case, the height of the projections 222 is appropriately set such that the metal particulates 222B of the opposing projections 222 are at the above-described gap within the width of the slit grooves 221, making it possible to form a stronger enhancing electric field.

In the sensor main body 20, if the target substance as a detection target enters the enhancing electric field 224, Raman scattering light including information on the frequency of the target substance is generated. Raman scattering light is enhanced by the enhancing electric field 224, and surface-enhanced Raman scattering light is generated. Therefore, even when the amount of target substance is small, Raman scattering light having strong signal intensity is obtained, thereby increasing detection sensitivity.

As shown in FIG. 1, the pressure sensor 25 is provided at the bottom 21A of the concave groove 21 of the sensor main body 20. The pressure sensor 25 is a sensor which detects whether or not the closed space is sealed. That is, if the finger is further pressed against the sensor main body 20 in a state where the finger is in close contact with the packing member 211, the packing member 211 which is an elastic member is elastically deformed, and the pressure inside the closed space increases. Meanwhile, if the finger is not in close contact with the packing member 211 and a gap is generated, gas inside the closed space leaks from the gap, such that, even when the packing member 211 is pressed, the pressure does not change or the amount of change in pressure decreases. Thus, the change in pressure is detected by the pressure sensor 25, making it possible to easily detect whether or not the closed space is sealed.

3. Configuration of Control Section

Figure 4:
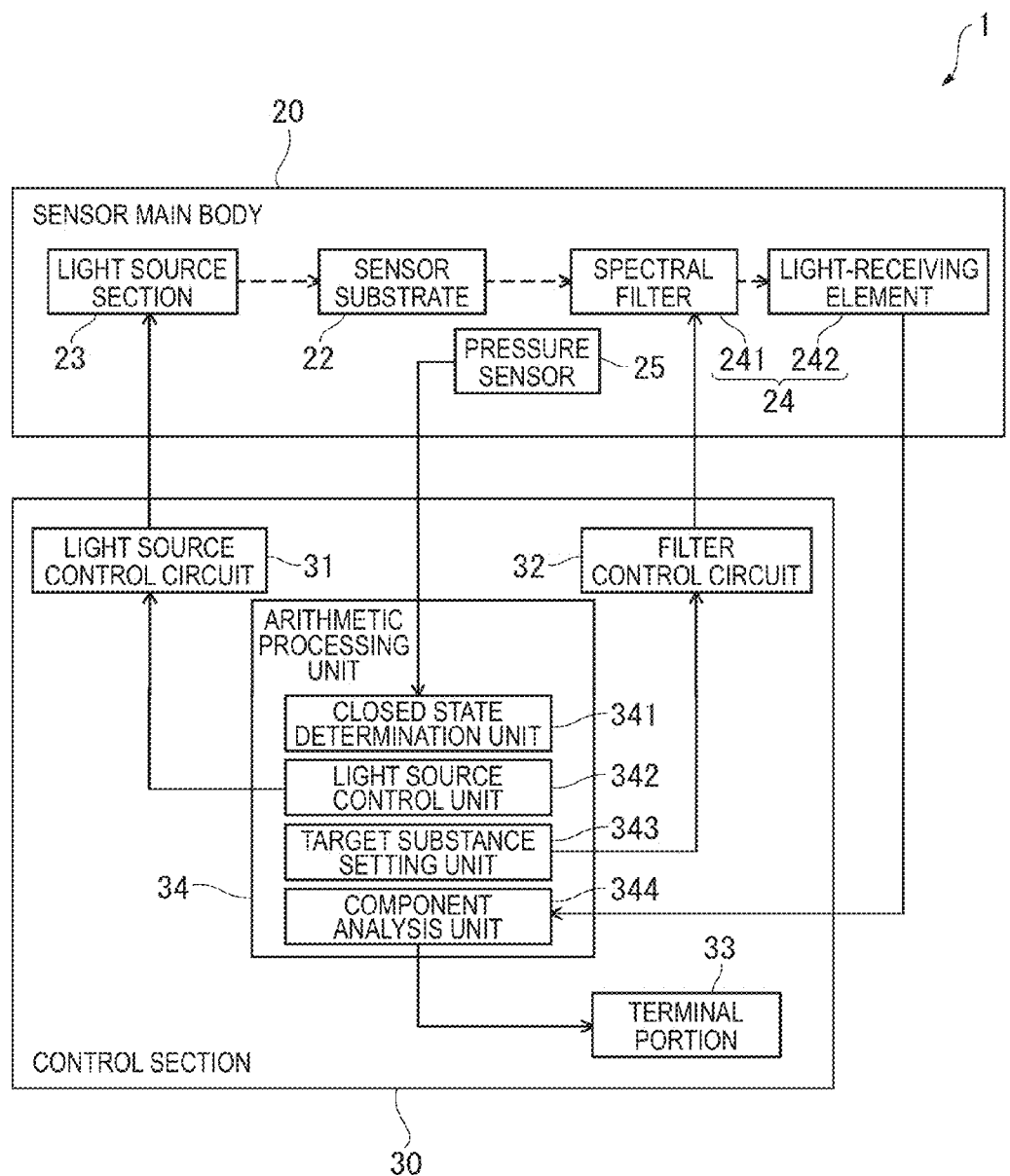
FIG. 4 is a block diagram showing the schematic configuration of a substance component detection device of the first embodiment.

FIG. 4 is a block diagram showing the schematic configuration of the substance component detection device 1 of the first embodiment.

As shown in FIG. 4, the control section 30 of the substance component detection device 1 includes a light source control circuit 31 which controls the light source section 23, a filter control circuit 32 which controls the spectral filter 241, a terminal portion 33 which is connectable to an external device, and an arithmetic processing section 34.

The light source control circuit 31 drives the light source section 23 on the basis of a detection start command input from the arithmetic processing section 34 to emit laser light toward the sensor substrate 22.

The filter control circuit 32 controls the spectral filter 241 on the basis of a filter control command input from the arithmetic processing section 34. For example, when the spectral filter 241 is a wavelength-variable etalon element which varies the gap between a pair of mirrors by voltage application to set a wavelength to transmit, a voltage according to the wavelength of Raman scattering light to be acquired is applied to the spectral filter 241.

The terminal portion 33 is connectable to, for example, an output device, such as a display or a printer, or an information processing device, such as a personal computer, and outputs analysis result information relating to the target substance analyzed by the arithmetic processing section 34.

The arithmetic processing section 34 is constituted by, for example, an arithmetic circuit, such as a CPU (Central Processing Unit), and a storage circuit, such as a memory, and appropriately executes a program stored in the memory to control the overall operation of the substance component detection device 1. Specifically, the arithmetic processing section 34 executes various programs, and as shown in FIG. 4, functions as a closed state determination unit 341, a light source control unit 342, a target substance setting unit 343, and a component analysis unit 344.

The closed state determination unit 341 determines whether or not the closed space is sealed on the basis of the pressure detected by the pressure sensor 25. As described above, in a state where the closed space is sealed by the finger, if the packing member 211 is pressed and elastically deformed, the pressure inside the closed space increases. Meanwhile, when the closed space is not sealed and a gap is generated, the pressure does not change or the amount of change in pressure is small. Thus, the closed state determination unit 341 monitors the change in the pressure detected by the pressure sensor 25, and when the pressure increases to be equal to or larger than a threshold value set in advance, specifies that the closed space is sealed.

The light source control unit 342 outputs a detection start command to the light source control circuit 31, such that laser light is emitted from the light source section 23.

The target substance setting unit 343 sets a target substance as an analysis target in skin gas. In this case, for example, a target substance is set on the basis of a signal input from an operation unit (not shown) separately provided in the substance component detection device 1. The target substance setting unit 343 outputs a filter control command to the filter control circuit 32, and sets the spectral filter 241 so as to transmit the wavelength of Raman scattering light corresponding to the set target substance.

Although in this embodiment, the target substance setting unit 343 controls the spectral filter 241 so as to transmit only Raman scattering light corresponding to the target substance, for example, when a single target substance in skin gas is a detection target, the process for setting a target substance in the target substance setting unit 343 may not be performed.

The component analysis unit 344 detects the target substance in skin gas on the basis of the intensity of Raman scattering light input from the light-receiving element 242. The content (concentration) of the target substance is calculated on the basis of the intensity of Raman scattering light. The component analysis unit 344 displays the concentration of the detected target substance on a display section (not shown) or outputs the concentration of the detected target substance from the terminal portion 33 to the external device.

4. Functional Effects of This Embodiment

In the substance component detection device 1 of the first embodiment, the concave groove 21 having the opening 21B is provided at the bottom 12A of the positioning concave portion 12 of the base portion 10. Inside the concave groove 21 are provided the sensor substrate 22, the light source section 23 which emits laser light toward the sensor substrate 22, and light-receiving section 24 which receives Raman scattering light generated by the sensor substrate 22. The sensor substrate 22 includes the projection group 223 which is constituted by a plurality of projections 222 having coated thereon the metal particulates 222B.

In the substance component detection device 1, the opening is closed by the finger, such that the inside the concave groove 21 becomes the closed space. Skin gas transpired from the finger is discharged and filled into the closed space. If laser light is irradiated from the light source section 23 to the projection group 223 of the sensor substrate 22, the enhancing electric field 224 is formed between the metal particulates 222B. In this sensor, if the target substance in skin gas enters the enhancing electric field 224, Raman scattering light of the target substance generated by laser light irradiated is enhanced and becomes surface-enhanced Raman scattering light. In the substance component detection device 1, surface-enhanced Raman scattering light is detected by the light-receiving section 24, thereby acquiring the intensity of Raman scattering light corresponding to the target substance.

The sensor substrate 22 is formed in a square shape having each side of 5 mm, and the projection group 223 formed in the sensor substrate 22 has a minute shape of about 1 nm to several tens of nm. The concave groove 21 is formed of a size to be closed by the pad portion of the finger. That is, the substance component detection device 1 can be reduced in size compared to other analysis devices, such as a chromatograph, and can have a simple configuration, thereby reducing the manufacturing cost of the device.

Since the device is fixed directly to the skin and detects the target substance, for example, it is not necessary to perform a complex operation to extract skin gas and analyze skin gas by an analysis device, and it is possible to easily detect the target substance in skin gas.

The substance component detection device 1 includes the packing member 211 which is provided along the opening 21B of the concave groove 21. For this reason, when the finger is placed in the concave portion 12, the packing member 211 and the finger are in close contact with each other, such that the closed space inside the concave groove 21 can be sealed, thereby preventing leakage of skin gas.

As the seal member according to the invention, the packing member made of an elastic member, such as rubber, is used. For example, when a member having no elasticity is used as the seal member, a gap may be generated in the wrinkled portion of the skin, and skin gas may leak from the closed space. While a liquid or gel-like material is applied as the seal member, in this case, if vaporized gas of the liquid or gel-like material enters the closed space, accurate target substance detection may not be performed. Since the liquid or gel-like material should be applied for each measurement, the operation may be complicated. In contrast, when the seal member is constituted by an elastic member, it is not necessary to perform an operation, such as application, and the closed space can satisfactorily become a sealed space with no vaporized gas from the seal member.

As described above, nonvolatile gel or the like may be applied to the packing member 211. In this case, while an operation at the time of detection is complicated because an application operation is performed, it is possible to more reliably eliminate the gap between the skin and the packing member 211, thereby further reliably sealing the closed space.

In the substance component detection device 1, the band 12B may be provided in the base portion 10. With this configuration, it is possible to press the finger placed in the concave portion 12 against the sensor main body 20, thereby more reliably bringing the finger and the sensor main body 20 into close contact with each other.

For this reason, it is possible to more reliably eliminate the gap between the finger and the opening 21B, and to prevent a problem in that a gap is generated in the closed space and skin gas leaks. In order to prevent leakage of skin gas, it is not necessary to perform an operation or the like to press the finger against the sensor main body, and it is possible to more easily perform the process for detecting the target substance in skin gas.

In this embodiment, the sensor substrate 22 is provided such that the surface in which the projection group 223 is provided faces the opening 21B. The sensor substrate 22 is also provided in parallel with the opening surface 21B1 of the opening 21B.

With this configuration, it is possible to make the depth of the concave groove 21 small, and to suppress an increase in the thickness of the substance component detection device 1. Since the projection group 223 faces the opening 21B, the target substance in skin gas transpired from the finger easily enters between the projections 222 of the projection group 223, thereby improving detection efficiency of the target substance. Since the distance between each projection 222 of the projection group 223 and the finger is made uniform, concentration of the target substance inside the projection group 223 hardly occurs.

The sensor main body 20 includes the pressure sensor 25 which detects the pressure of the closed space. The closed state determination unit 341 of the control section 30 determines whether or not the closed space is sealed on the basis of the change in the pressure detected by the pressure sensor 25.

For this reason, the finger is in close contact with the packing member 211, and it is possible to easily determine whether or not the closed space is sealed. It is also possible to prevent the process for detecting the target substance in a state where skin gas is leaking, thereby performing an accurate detection process.

Although in this embodiment, the component analysis unit 344 of the control section 30 in the substance component detection device 1 performs the component detection of the target substance and the concentration measurement of the detected component from the intensity of Raman scattering light detected by the sensor main body 20, the invention is not limited thereto. That is, the substance component detection device 1 may be a device which acquires and outputs Raman scattering light detected by the sensor main body 20, and outputs the intensity of acquired Raman scattering light from the terminal portion 33 to the external device.

Second Embodiment

Next, a second embodiment of the invention will be described with reference to the drawings.

Figure 5:
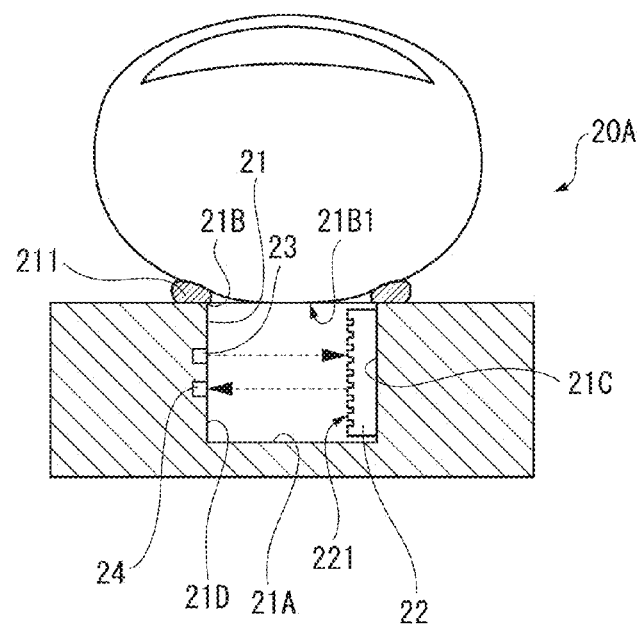
FIG. 5 is a schematic sectional view of a sensor main body of a second embodiment.

FIG. 5 is a schematic sectional view of a sensor main body 20A of the second embodiment. In the following description of the embodiments, the same parts as those in the first embodiment are represented by the same reference numerals, and description thereof will not be repeated or will be simplified.

In the sensor main body 20 of the first embodiment, the sensor substrate 22 is provided in parallel with respect to the opening surface 21B1 of the opening 21B of the concave groove 21. In contrast, in the sensor main body 20A of the substance component detection device of the second embodiment, as shown in FIG. 5, the sensor substrate 22 is provided in an inner circumferential lateral surface 21C of the concave groove 21. That is, the sensor substrate 22 is provided such that the surface in which the projection group 223 (see FIG. 3) is provided is perpendicular to the opening surface 21B1 of the opening 21B.

The light source section 23 and the light-receiving section 24 are provided in an inner circumferential lateral surface 21D facing the inner circumferential lateral surface 21C in which the sensor substrate 22 is provided.

Functional Effects of Second Embodiment

With this configuration, laser light emitted from the light source section 23 is incident at an incidence angle perpendicular to or substantially perpendicular to the projection group 223 of the sensor substrate 22. In this way, laser light is incident at an angle substantially perpendicular to the sensor substrate 22 in which the projection group 223 is provided, thereby suppressing the amount of light loss of laser light.

The light-receiving section 24 is provided in the inner circumferential lateral surface 21D facing the surface of the sensor substrate 22 in which the projection group 223 is provided. With this configuration, since the distance from the enhancing electric field 224 formed between the projections 222 of the projection group 223 to the light-receiving section 24 is made uniform, it is possible to accurately detect the intensity of Raman scattering light in each enhancing electric field 224 inside the projection group 223.

In particular, when calculating the concentration of the target substance from Raman scattering light, it is preferable to calculate the concentration in accordance with the number of generation positions of Raman scattering light, the area of the generation position, or the like. That is, since the intensity of Raman scattering light generated in one enhancing electric field 224 changes depending on the position of the target substance inside the enhancing electric field 224, or the like, the concentration of the target substance and the intensity of Raman scattering light is not necessarily limited to a proportional relationship. In contrast, the concentration of the target substance and the number of generation positions of the Raman scattering light or the area of the generation position substantially have a proportional relationship. Therefore, as described above, the light-receiving section 24 is provided to face the surface of the sensor substrate 22, in which the projection group 223 is provided, such that the distance from each projection 222 is substantially made uniform, such that the generation positions of Raman scattering light (the distribution of the generation positions of Raman scattering light) generated within the plane can be satisfactorily acquired, thereby detecting the concentration of the target substance.

Third Embodiment

Next, a substance component detection device according to a third embodiment of the invention will be described.

Figure 6:
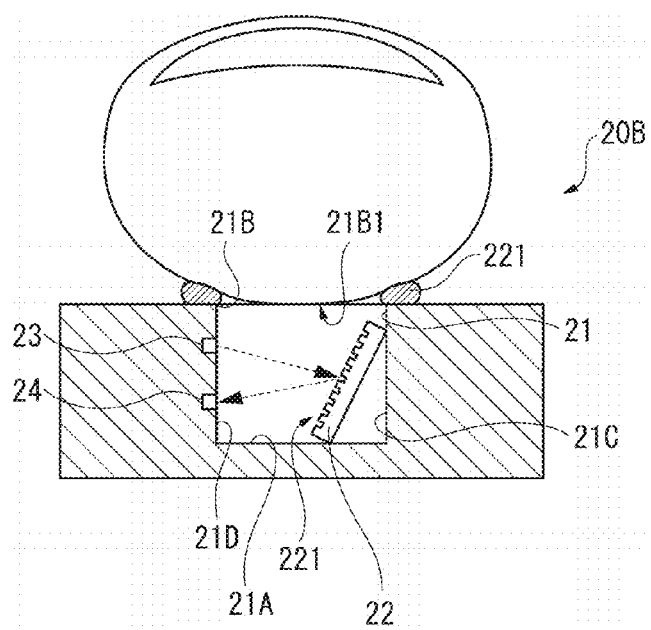
FIG. 6 is a schematic sectional view of a sensor main body of a third embodiment.

FIG. 6 is a sectional view schematically showing a sensor main body of the third embodiment.

In the substance component detection device 1 of the second embodiment, the sensor substrate 22 is provided such that the sensor main body 20A is perpendicular to the opening surface 21B1 of the opening 21B along the inner circumferential lateral surface 21C of the concave groove 21. In contrast, like a sensor main body 20B shown in FIG. 6, the sensor substrate 22 may be placed to be inclined with respect to the opening surface 21B1 of the opening 21B.

It is preferable that the sensor substrate 22 is set an angle equal to or larger than 45 degrees and smaller than 90 degrees with respect to the opening surface 21B1 of the opening 21B (in the case of 90 degrees, the configuration is the same as in the second embodiment). That is, when the inclination angle of the sensor substrate 22 is equal to or larger than 0 degree and smaller than 45 degrees, the incidence angle of laser light incident on the sensor substrate 22 from the light source section 23 decreases, and the amount of light loss of laser light increases. In contrast, when the sensor substrate 22 is provided at equal to or larger than 45 degrees and smaller than 90 degrees, it is possible to adjust the emission angle of laser light of the light source section 23 such that the incidence angle of laser light becomes close to the normal direction of the sensor substrate 22. Therefore, as in the second embodiment, it is possible to intensify the enhancing electric field 224 in the projection group 223 (see FIG. 3), making it possible to increase detection precision.

Functional Effects of Third Embodiment

In the third embodiment, the sensor substrate 22 is provided at an angle equal to or larger than 45 degrees and smaller than 90 degrees with respect to the opening surface 21B1 of the opening 21B.

For this reason, it is possible to allow laser light to be incident at an incidence angle perpendicular to or substantially perpendicular to the projection group 223 of the sensor substrate 22, to suppress the amount of light loss of laser light, and to intensify the enhancing electric field 224.

The light-receiving section 24 is provided at a position such that the distance to each projection 222 is made uniform, thereby accurately detecting the intensity of Raman scattering light in each enhancing electric field inside the projection group 223, to satisfactorily acquire the distribution of the generation positions of the Raman scattering light generated within the plane, and to detect the concentration of the target substance with satisfactory precision.

It is also possible to make the depth of the concave groove 21 small compared to the second embodiment, thereby promoting the reduction in size of the substance component detection device.

Fourth Embodiment

Next, a fourth embodiment of the invention will be described with reference to the drawings.

Figure 7:
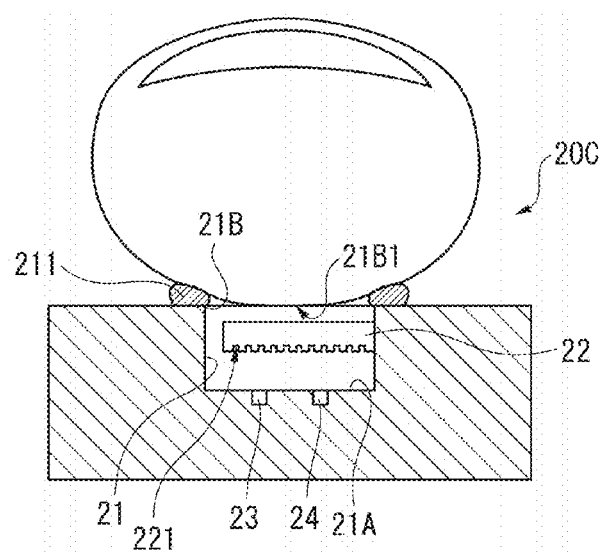
FIG. 7 is a schematic sectional view of a sensor main body of a fourth embodiment.

FIG. 7 is a sectional view schematically showing a sensor main body of the fourth embodiment.

Although in the foregoing first embodiment, the sensor substrate 22 is arranged such that the surface in which the projection group 223 is provided faces the opening surface 21B1 of the opening 21B, in the fourth embodiment, as shown in FIG. 7, the sensor substrate 22 is arranged such that the projection group 223 (see FIG. 3) faces the bottom 21A of the concave groove 21.

In a sensor main body 20B, a slight gap is formed between the sensor substrate 22 and the bottom 21A such that skin gas enters. In the sensor main body 20B, the light source section 23 and the light-receiving section 24 are provided at the bottom 21A of the concave groove 21, emit laser light toward the projection group 223 facing the bottom 21A, and receives Raman scattering light emitted toward the bottom 21A.

Functional Effects of Fourth Embodiment

In the fourth embodiment, since the sensor substrate 22 is provided in parallel with respect to the opening surface 21B1 of the opening 21B, as in the foregoing first embodiment, it is possible to make the depth of the concave groove 21 small and to make the thickness of the substance component detection device small, thereby promoting the reduction in size of the device.

Since the light source section 23 and the light-receiving section 24 are provided at the bottom 21A, and face the projection group 223 of the sensor substrate 22, as in the second embodiment and the third embodiment, it is possible to allow laser light to be irradiated at an incidence angle perpendicular to the sensor substrate 22, and to further intensify the enhancing electric field 224. In the light-receiving section 24, it is possible to detect the distribution of Raman scattering light within the plane of the projection group 223 with satisfactory precision.

In the configuration in which the light source section 23 and the light-receiving section 24 are provided in the inner circumferential lateral surface of the concave groove 21, when the depth of the concave groove 21 is small, arrangement is not easily performed. In contrast, in this embodiment, since the light source section 23 and the light-receiving section 24 are provided at the bottom 21A, it is possible to secure a sufficient arrangement space of the light source section 23 and the light-receiving section 24, thereby easily arranging the light source section 23 and the light-receiving section 24.

Other Embodiments

The invention is not limited to the foregoing embodiments, and modifications, improvements, and the like within the scope in which the object of the invention can be achieved still fall within the scope of the invention.

For example, although in the foregoing embodiment, the finger of the measurement-target person is a measurement site in the substance component detection device 1, the invention is not limited thereto.

The substance component detection device may be in contact with any measurement site, such as a palm, an arm, or a leg, insofar as skin gas of a person is detected. Of these, the finger or palm is particularly preferable because skin is usually exposed and the measurement-target person can easily perform measurement.

Although the concave groove 21 provided in the base portion 10 is used as a closed space forming portion of the sensor main body 20, the invention is not limited thereto. For example, a cylindrical projecting portion may be formed on the base portion 10, and the tip of the projecting portion may be in contact with the skin of the measurement-target person, such that a closed space is formed on the inner circumference of the cylinder.

Although the light source section 23 which emits laser light is provided directly in the lateral surface of the concave groove 21 as an incidence optical system, the invention is not limited thereto. An optical system may be provided which guides laser light from a window portion provided in the lateral surface of the concave groove 21 toward the sensor substrate 22. Similarly, with regard to the light-receiving section 24, an optical system may be provided which guides Raman scattering light incident on the window provided in the lateral surface of the concave groove 21 to the light-receiving element.

Although the configuration has been described in which the slit grooves 221 are formed in the sensor substrate 22, a configuration may be made in which only the projection group 223 having a plurality of projections 222 are provided without forming the slit grooves 221.

Although the projections 222 are constituted by coating the metal particulates 222B on the convex portions 222A, for example, the projections 222 may be constituted by only the spherical metal particulates 222B. In this case, for example, a configuration may be made in which slits which are smaller than the diameter of the metal particulates 222B are arranged in the surface of the sensor substrate 22 at an interval smaller than the laser oscillation wavelength, and the metal particulates 222B are held on the slits.

Although the wavelength-variable etalon element which can select the wavelength to transmit is used as the spectral filter 241 of the light-receiving section 24, for example, a band-pass filter which transmits only a specific wavelength of Raman scattering light may be used.

Although in the foregoing embodiments, the concave groove 21 having the single opening 21B is used as the closed space forming portion, the invention is not limited thereto.

Figure 8:
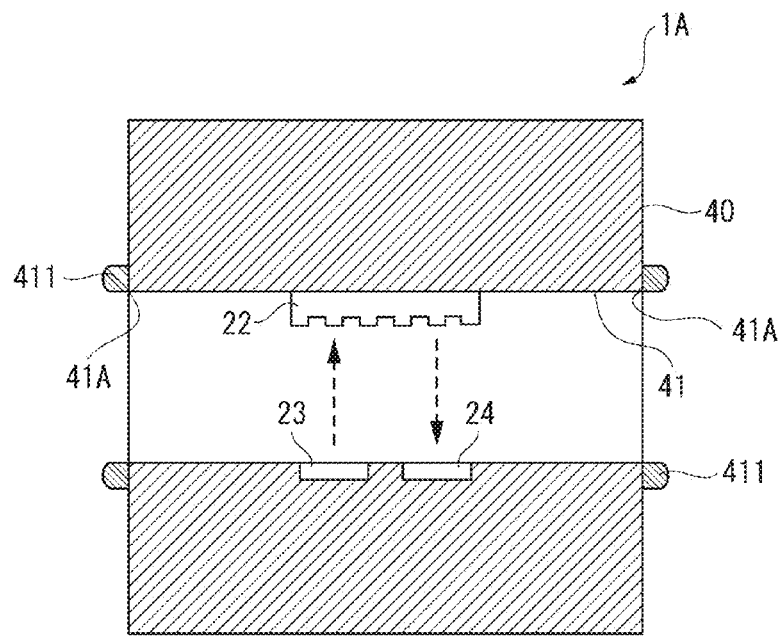
FIG. 8 is a sectional view showing the schematic configuration of a substance component detection device according to another embodiment.

For example, as shown in FIG. 8, a through hole 41 having a cylindrical inner circumferential surface may be formed in the base portion 40, and the through hole 41 may constitute the closed space forming portion according to the invention. In this case, as shown in FIG. 8, packing members 411 serving as a seal member are provided along the opening edges of the openings 41A at both ends of the through hole 41, and the sensor substrate 22, the light source section 23, and the light-receiving section 24 are provided inside the through hole 41.

In a substance component detection device 1A configured as above, the openings 41A at both ends of the through hole 41 are sandwiched by fingers, such that the inside of the through hole 41 becomes a sealed closed space. In this case, the openings 41A at both ends of the through hole 41 are closed by the skin, and the amount of skin gas discharged into the closed space increases, thereby improving detection precision of the target substance in skin gas.

Although the bet configuration for carrying out the invention has been specifically described, the invention is not limited thereto. That is, while the invention has been mainly shown and described in connection with the specific embodiments, those skilled in the art can make various modifications and improvements to the foregoing embodiments without departing from the technical spirit and scope of the invention.

The entire disclosure of Japanese Patent Application No. 2011-061226, filed Mar. 18, 2011 is expressly incorporated by reference herein.

What is claimed is:

1. A substance component detection device comprising:
a sensor substrate which is provided in a closed space of a closed space forming portion, which has at least one opening and in which the opening is adapted to be closed by a measurement-target skin such that the inside of the closed space forming portion forms the closed space, the sensor substrate having a projection group having a plurality of metal projections;

an incidence optical system which emits light toward the projection group; and a light-receiving section which detects Raman scattering light generated by the projection group, wherein the closed space forming portion includes a plurality of lateral surfaces, the incidence optical system being provided on a section on at least one lateral surface and emitting the light toward at least an opposite lateral surface, wherein the opening is defined by the top of each lateral surface of the closed space forming portion.

2. The substance component detection device according to claim 1, wherein a seal member which is adapted to be in close contact with the skin along the opening to seal the closed space is provided in the closed space forming portion.

3. The substance component detection device according to claim 2, wherein the seal member is an elastic member.

4. The substance component detection device according to claim 1, further comprising:

a pressing unit which is adapted to press the skin against the closed space.

5. The substance component detection device according to claim 1, wherein the sensor substrate is provided at an angle crossing an opening surface, which is a surface including the opening edge of the opening.

6. The substance component detection device according to claim 5, wherein the sensor substrate is provided at an angle equal to or larger than 45 degrees and equal to or smaller than 90 degrees with respect to the opening surface.

7. The substance component detection device according to claim 1, wherein the sensor substrate is provided in parallel with respect to an opening surface, which is a surface including the opening edge of the opening.

8. The substance component detection device according to claim 7, wherein the sensor substrate is provided in a state where the projection group faces the opening surface.

9. A substance component detection device comprising:

a sensor substrate which is provided in a closed space of a closed space forming portion, which has at least one opening and in which the opening is adapted to be closed by a measurement-target skin such that the inside of the closed space forming portion forms the closed space, the sensor substrate having a projection group having a plurality of metal projections;

an incidence optical system which emits light toward the projection group; and a light-receiving section which detects Raman scattering light generated by the projection group, wherein the closed space forming portion includes a plurality of lateral surfaces, wherein the opening is defined by the top of each lateral surface of the closed space forming portion;

wherein the sensor substrate is provided in parallel with respect to an opening surface, which is a surface including the opening edge of the opening;

wherein the closed space forming portion includes a bottom portion which faces the opening, the sensor substrate is provided in a state where the projection group faces the bottom portion, a gap through which skin gas transpired from the skin is passable is provided between the sensor substrate and the bottom portion, and the incidence optical system and the light-receiving section are provided in the bottom portion.

\* \* \* \* \*